United States Patent [19]

Ecanow et al.

[11] Patent Number: 4,738,952

[45] Date of Patent: * Apr. 19, 1988

[54] SUBSTITUTE FOR HUMAN BLOOD AND A METHOD OF MAKING THE SAME

[75] Inventors: Bernard Ecanow, Wilmette; Charles S. Ecanow, Skokie, both of Ill.

[73] Assignee: Synthetic Blood Corporation, Deerfield, Ill.

[*] Notice: The portion of the term of this patent subsequent to Mar. 27, 2001 has been disclaimed.

[21] Appl. No.: 811,675

[22] Filed: Dec. 20, 1985

Related U.S. Application Data

[63] Continuation-in-part of Ser. No. 604,476, Apr. 27, 1984, abandoned.

[51] Int. Cl.$^4$ .............................................. A61K 37/00
[52] U.S. Cl. ............................................ 514/6; 514/2
[58] Field of Search .................................... 514/2, 6

[56] References Cited

U.S. PATENT DOCUMENTS

| | | |
|---|---|---|
| 3,169,094 | 2/1965 | Wretlind . |
| 4,133,874 | 1/1979 | Miller et al. . |
| 4,252,793 | 2/1981 | Altman . |
| 4,321,259 | 3/1982 | Nicolau et al. . |
| 4,343,797 | 8/1982 | Ecanow et al. . |

FOREIGN PATENT DOCUMENTS

| | | |
|---|---|---|
| 0083469 | 7/1983 | European Pat. Off. . |
| 8401717 | 10/1984 | PCT Int'l Appl. . |

OTHER PUBLICATIONS

*Blood Policy & Technology*, Jan. 1985, Office of Technology Assessment, pp. 136-150.
Gessner G. Hawley, ed., The Condensed Chemical Dictionary, 9th ed., (New York: Van Nostrand Reinhold Company, 1977). p. 213.
Arthur Osol, ed., *Remington's Pharmaceutical Sciences*, (Easton, Pa.: Mack Publishing Co., 1975), p. 315.
J. McMullen et al., "Pectin-Gelatin Complex Coacervates", *Journal of Pharmaceutical Science*, vol. 71, No. 6, (Jun., 1982), pp. 628-633.
A. Veis and C. Aranyi, "Phase Separation in Polyelectrolyte Sytems", *Journal of Physical Chemistry*, vol. 64, (1960), pp. 203-210.
Dowben, Robert M., *General Physiology, A Molecular Approach*, Harper & Row, N.Y., 1969, pp. 146-147.
Considine, D. M., *Van Nostrand's Scientific Encyclopedia*, 6th ed., Van Nostrand Reinhold Co., N.Y., 1983, pp. 1769-1770.
Watanabe et al., Chemical Abstracts, vol. 81, (1974), p. 16715v.
Kaplan et al., Chemical Abstracts, vol. 83, (1975), p. 53540w.
Vinograd-Finkel et al., Chemical Abstracts, vol. 77, (1972), p. 86318j.
E. Selkurt, ed., *Physiology*, 2nd ed., (Boston: Little, Brown & Co., 1966), p. 216.
A. Guyton, *Basic Human Physiology: Norman Functions and Mechanisms of Disease*, (Philadelphia: W. B. Saunders Co., 1971), p. 157.
M. Ashwood, "Polyvinylpyrolidone Solutions Used in Plasma Expanders: Potential Carcinogens?", *The Lancet*, (1971), p. 1304.
R. A. Kahn et al., "Alternative Source and Substitutes for Therapeutic Blood Sources", *Blood*, Journal of the American Society of Hematology, vol. 66-1, (Jul., 1985), pp. 1-12.
C. Tabor, *Tabor's Cyclopedic Medical Dictionary*, (Philadelphia, Pa., F. A. Davis Co., 1977), pp. H21-22.
Merck Manual, 14th ed., (Rahway, N.J.: Merck & Co., Inc.), 1982.
"Blood", *Van Nostrand's Scientific Encyclopedia*, 1968, pp. 214-215.
Documenta Geigy, (Basel, Switzerland: J. R. Geigy, 1956).
*Geigy Scientific Tables*, 8th ed., (Basel, Switzerland: Ciba-Geigy, Ltd., 1982).
Department of Defense, Document No. 84-R-0033, p. 7.
Ostra, Liposomes, (New York: Marcelle-Deeker, 1980).
R. Bucala et al., "Cytotoxicity of a Perfluorocarbon Blood Substitute to Macrophages in Virto", *Science*, vol. 220, (May, 1983), pp. 965-967.
P. Lundsgaard-Hansen, M.D. and B. Tschirren, M.D., "Modified Fluid Gelatin as a Plasma Substitute", *Blood Substitutes and Plasma Expanders*, (New York: Alan R. Liss, 1978), p. 227.
Ashwood-Smith, M. S., "Polyvinyl-Pyrolidone Solutions Used in Plasma Expander Potential Carcinogens"; *Lancet*, 1, (1971), p. 1304.
Towers, R. P., "Lymph Node Changes Due to Polyvinyl-Pyrolidone", *Journal of Clinical Pathology* 10, (1975-1977), p. 1957, BF1400.A1J83.
F. DeVenuto et al., "Preparation and Evaluation of Pyridoxalated Polymerized Human Hemoglobin", *Journal of Surgical Research*, vol. 34, pp. 205-212, (1983).

*Primary Examiner*—Sam Rosen
*Attorney, Agent, or Firm*—Mason, Kolemainen, Rathburn & Wyss

[57] ABSTRACT

The method of this invention yields a two phase liquid aqueous system which replicates the two phase heterogeneous physiochemical system of naturally occurring whole human blood. The method produces a composition of matter which comprises a whole blood substitute when polymerized hemoglobin or pyridoxylated-polymerized hemoglobin and preferably, other specific additives are incorporated. When said blood substitute is processed further, a microencapsulated composition with time release characteristics that can transport oxygen is produced. The invention overcomes the obstacles that have prevented the use of modified hemoglobins like pyridoxylated-polymerized hemoglobin in the preparation of oxygen transport systems.

41 Claims, No Drawings

SUBSTITUTE FOR HUMAN BLOOD AND A METHOD OF MAKING THE SAME

This is a continuation-in-part of our application Ser. No. 604,476 filed Apr. 27, 1984, now abandoned.

The invention concerns an improved composition useful as a substitute for human blood and as an oxygen transport system, and methods of prepartion.

DESCRIPTION OF THE PRIOR ART

In response to an evident need, a number of oxygen transporting solutions have recently been developed. Each reflects a different approach. At this point of development, most of these preparations exhibit either manufacturing or clinical difficulties. In some instances, both problems are present.

Perfluorocarbon based compositions were among the earliest of these oxygen transport solutions. While such compositions posses oxygen carrying capability, difficulties in dwell time, in administering the preparation and the suspicion of a toxic potential has raised serious questions regarding the safety and utility of this product.

The effort to replicate erythrocytes through the development of liposomes containing stroma free hemoglobin represents a second approach. (Ref. Djorejevich, L; Miller, L. "Lipid Encapsulated Hemoglobin as a Synthetic Erythrocyte," Fed. Proc. 1977, 36:567). The evidence to date suggests that in this approach, undesireable and erratic effects are known to follow when the hemoglobin of the composition attaches to the exterior of the liposome during the process of manufacture or leaks from the encapsulating liposome after the product is introduced into the circulation of the recipient. In either event, free hemoglobin is liberated into the circulation of the recipient. The possible consequences of this event are well known to clinicians and other skilled in the art.

A third approach to the development of an oxygen transporting fluid is based upon efforts to modify the hemoglobin molecule through the process of pyridoxylation and polymerization. See: DeVenuto, F. and Zegna, A., "Preparation and Evaluation of the Pyridoxalated-Polymerized Hemoglobin Molecule". *Journal of Surgical Research,* Vol. 34, p. 205–212, (1983).

At least two major difficulties, appear to be associated with solutions containing modified hemoglobin. The first involves the problem of oxygen release; the second is the loss of the composition from the vascular space. The problem of the toxicity of this composition has apparently not been explored. These difficulties raise doubts about the utility of presently known oxygen transporting solutions based on modified hemoglobin.

The fourth approach to the development of an oxygen transporting solution is based upon the applicants' inventions disclosed in U.S. Pat. Nos. 4,343,797 and 4,439,424. The process involved in this approach makes use of a two phase liquid aqueous heterogeneous system and yeilds a substitute for human blood.

SUMMARY OF THE INVENTION

The herein disclosed invention represents a significant scientific advance in that through its use of a coacervate system the problems associated with unmodified hemoglobin solutions, polymerized hemoglobins and pyridoxylated-polymerized hemoglobin, are avoided.

The manufacturing sequence of this invention is designed: (1) to yield a coacervate system which can serve as a whole blood substitute with the incorporation of polymerized hemoglobin or pyridoxylated-polymerized hemoglobin; and (2) to provide, if desired, a form of microencapsulated hemoglobin with an approximate equivalence to the cytoplasm of erthrocytes or packed red cells. The oxygen carrying solution herein described can also restore and maintain normal oncotic pressure when infused into the circulatory system.

For purposes of this application, the applicants draw a distinction between synthetic blood products disclosed in U.S. Pat. Nos. 4,343,797 and 4,439,424, and oxygen transport solutions. For the most part the oxygen release curve of the latter differs significantly from that of the prior art.

It is an object of this invention to provide a composition of matter which can serve as a whole blood substitute. It can serve as a substitute for human blood. It is another object to provide a convenient method for the manufacture of these compositions based on the process of coacervation. It is a further object to provide a composition that has physiological characteristics equivalent to those of packed red cells, and further a convenient method of preparing this composition. Moreover this invention provides a composition with characteristics similar to the cytoplasm of erythrocytes and a method of producing the same.

DETAILED DESCRIPTION OF THE INVENTION

In particular, the invention provides a composition of matter which is useful as a whole blood substitute; said preparation characterized by a non-toxic two phase liquid system, both said phase being aqueous (a) one of said phases being relatively nonpolar coacervate phase having physiological and physicochemical properties substantially equivalent to cytoplasm, as present in red blood cells;

(b) the other of said phases being a relatively polar liquid aqueous phase having physiological and physicochemical properties substantially equivalent to blood plasma;

(c) said relatively non-polar coacervate phase being insoluble in and in equilibrium with said relatively polar liquid aqueous phase, (d) an incorporated into said two phase system having a modified hemoglobin component selected from polymerized hemoglobin, pyridoxylated-polymerized hemoglobin, or mixtures thereof, (e) said two phase system having physiological and physico-chemical properties substantially similar to whole blood.

Moreover the invention provides a method of preparing a composition of matter which is useful as a blood substitute, said method characterized by the steps of (a) combining albumin anad a phospholipid in water; (b) thoroughly mixing the components; (c) storing said mixture undisturbed until the composition of step (a) separates into two layers, one above the other, the lower layer being a substantially non-polar coacervate phase, and the upper layer being an equilibrium water phase; (d) continuing the separation process until no increase in the volume of the coacervate phase can be observed; (e) centrifuging the composition until inspection reveals a clear demarcation of the two phases; and (f) separating the two phases and (g) adding a modified hemoglobin solution to the system selected from polymerized hemoglobin, pyridoxylated-polymerized hemoglobin or mixtures thereof.

This invention comprises compositions of matter and methods by means of which they can be prepared. The claimed inventions comprise a combination of endogenous components and water which yields a two phase heterogeneous physico-chemical coacervate system similar to that of human blood. This coacervate system is the basis of the herein disclosed discovery.

In practice, any appropriate non toxic coacervate system can be used to manufacture the products of this invention, and further, any endogenous biological surface active agent or derivative thereof, such as albumin, lecithin, gelatin etc., can be used to prepare a coacervate system appropriate for the method and product of this invention. Appropriate non-toxic exogenous components, i.e. acacia gel, can also be used to prepare suitable coacervate systems.

The method of making this invention begins with the preparation of a two phase aqueous liquid system, also referred to as a coacervate system. When the preparation of the coacervate system is completed, it wil consist of two phases: (1) an internal suspension, relatively non polar phase, commonly referred to as the coacervate phase; and (2) an associated, relatively polar external suspension or equilibrium phase. Both phases are in equilibrium with and insoluble in each other. The coacervate phase of this two phase system can comprise from about 0.5% to 99.5% by volume of the system; correspondingly, the associated equilibrium phase can comprise from about 0.5% to 99.5% by volume of the system. The preferred proportions are 50% volume to volume of each of these components. The hemoglobin component is incorporated into the two phase system.

The coacervate phase of the claimed coacervate system possesses physiological porperties equivalent to the cytoplasm of erythrocytes or packed red cells. As such, this phase of the coacervate system has significant oxygen transport capability. The equilibrium phase possesses physiological and physiochemical properties equivalent to the plasma of human blood.

The claimed two phase aqueous liquid system, (i.e. coacervate system) functions incorporating specific hemoglobin components, as a whole blood substitute and may be drawn off during the process of manufacture. When components such as appropriate proteins, electrolytes, sterols, any of several available forms of hemoglobin and an oxygen releasing entity are added to the coacervate system, the system achieves a biochemical equivalence approaching that of human blood. If a composition with properties similar to the cytoplasm of erytrocytes or of packed red cells is desired, the dislcosed coacervate system and additives are subjected to warming and/or other procedures. In such process the end product is microencapsulated hemoglobin. The polymerized hemoglobin and pyridoxylated-polymerized hemoglobin used in the invention is based on human and other forms of mammalian blood, i.e. bovine blood, etc. The human source is preferred.

When modified hemoglobin, i.e., the pyridoxalated-polymerized form, is incorporated in the claimed preparation, the problems presently associated with such forms of hemoglobin, i.e. oxygen release, at normal oxygen tensions and loss of hemoglobin solution from the vascular system, are eliminated. This is enhanced through the addition of an oxygen releasing molecule, such as di-phospho-glycerate to the coacervate system in the course of the manufacturing process. As used in this invention, di-phospho-glycerate acts to release oxygen from hemoglobin precisely as it does in the body. Small quantities of urea may also be added, if desired, during the preparation of this composition to further the release of oxygen from the said composition.

Loss of the oxygen transport solution from the vascular space is prevented in this invention by two factors: (1) by emulsifying the preparation wherein the resulting emulsified droplets in which the hemoglobin is contained are manufactured to a size of approximately 7 microns, i.e., the size of normally occurring erythrocytes. Emulsified droplets of this size permit oxygenation of tissues, prevent escape of the solution from the circulation and allow entry of the hemoglobin bearing droplets into the microcirculation. The method of preparation, however, provides for the droplet size, if desired, to vary from 100 millimicrons to 15 microns.

Loss of the solution from the vascular space is also prevented in this invention through the effects of electrical charges present on the surface of droplets of the finished product and on the surfaces of arterial and venous branches of the circulatory system. Thus, the surfaces of blood vessels are negatively charged; the electrical charge on the surface of the emulsified droplets of the claimed composition is also negative. The resultant repulsant effect serves to prevent the loss of the solution from the circulatory system.

In the finished product, the composition may by comprised of emulsified droplets of the same size or of any combination of sizes, depending upon the intended use. Thus, in a given version of this invention a preponderance of emulsified droplets of a size smaller than 0.6 microns may be indicated; example: when it is desired that the claimed composition penetrate infarcted area(s) in the vascular system.

While the disclosed invention indicates that equal proportions of albumin and lecithin are preferred in the preparation of the claimed composition, it is possible to produce coacervate systems using unequal proportions of albumin and lecithin. In the case of such usage, however, the resulting coacervate system may not have the optimal yield of the coacervate phase. However, the coacervate phase of such systems may possess other desireable characteristics known to those skilled in the art, e.g., oxygen transport.

The claimed invention also contains a process in the manufacturing procedure which yields derivative compositions. One of these is the physiological equivalent of the cytoplasm of erythrocytes. When hemoglobin is added to this preparation, the equivalent of packed red cells is produced. The derivative preparations can be subjected to microencapsulation procedures and to a heating step. The heating step will act to harden the surface of the coacervate phase droplets of the composition to any desired degree. This results in compositions with sustained release characteristics. If desired, a chemical process using non-toxic members of the aldehyde group may be used. The heating procedure is preferred.

With the exception of the inventor's contribution to the prior art, the scientific literature contains no reference to a two phase heterogeneous physicochemical system which permits the effective incorporation of modified forms of hemoglobin and further, which can serve as a useful substitute for human blood. In addition, there is no literature reference to a composition which possesses physico-chemical properties that approximate those of the cytoplasm of erythrocytes or of packed red cells.

In order to explain the claimed invention, the following is a general example of a preferred method of preparation. Specific examples appear in the following section of this disclosure.

In the preparation of the disclosed composition, the component ingredients are prepared and combined under sterile conditions. All water used in the manufacturing process must be sterile and pyrogen free.

The preparation of the appropriate coacervate system constitutes the first step of the method necessary to produce the product of this invention. The preferred ingredients of this step are albumin and a suitable phospholipid. In this method lecithin is preferred. However, other phospholipids known to those skilled in the art such as cephalin, isolecithin, sphingomyolin, phosphatidyl serine, phosphatidic acid, phosphatidyl inosital, phosphatidyl choline may also be used.

In the preferred method, equal weight to volume proportions of albumin and lecithin are added to an amount of sterile water that will yield 100 mls. of aqueous solution. The mixture is then thoroughly mixed by vortex mixer. The preferred proportions for each component, i.e. albumin and lecithin, are 3% weight to volume. Unequal proportions of albumin and lecithin can yield a coacervate system. However, this method is not preferred.

In the preferred method of preparation any quantity of albumin and lecithin can be used, provided the requirement of the proportions of the ingredients is observed and quantity of water used is adjusted accordingly.

Following thorough mixing the solution is stored in suitable containers. In the preferred method, the solution is stored undisturbed until the maximum yield of the coacervate phase of the coacervate system has been achieved. Maximum yield is the point at which no significant increase in the volume of the coacervate phase can be observed. This determination can be made by direct visual inspection or other suitable means. As is known to those skilled in the art, longer periods of storage produce greater yields of the coacervate phase.

The storage step may take place at temperatures ranging from freezing point to about 4 degrees C. and up to room temperature or higher. In the preferred method, storage takes place at a temperature of from about 4 degrees to 10 degrees C.

When it is observed that the maximum yield of the coacervate phase has been achieved, the coacervate system is centrifuged until observation indicates that a clear division exists at the interface of the two phases of the coacervate system. If an oxygen transport solution is desired, the system is emulsified, the particle size of which may range from 100 millimicrons to 10 microns. The composition is placed in refrigerated storage until needed. If the manufacturing objective is to produce a synthetic blood, the following steps are initiated.

The two phases are then separated by means of a separatory funnel. The equilibrium phase is set aside for subsequent recombination with the coacervate phase. Any of the previously preferred to forms of hemoglobin is then mixed into the coacervate phase in an amount that will produce life sustaining oxygen tensions in the finished product. Suitable forms of the hemoglobin component are selected from polymerized hemoglobin, pyridoxylated-polymerized hemoglobin and mixtures thereof. In this disclosure pyridoxalated-polymerized hemoglobin is preferred. It is noted that the source of the hemoglobin component may be human or bovine.

After this step, any oxygen liberating entity, such as di-phospho-glycerate is added, and mixed into the coacervate phase. The amount added may range from 1% or less to 6% or more weight to volume. In this disclosure 4% weight to volume of di-phospho-glycerate is preferred.

The next step consists of recombining the equilibrium phase with the coacervate phase which now includes the additives described above. This is followed by a step in which the preparation is emulsified and an electrolyte is added. Any of the electrolytes known to those skilled in the art, i.e. sodium chloride, potassium chloride, magnesium chloride, or calcium chloride may be used. The purpose of this addition is to render the composition isotonic with human blood. Sodium chloride is the preferred electrolyte and is added in that quantity that will produce the desired isotonicity. At this point, if desired, 1 mg per cent of urea may be added. This component can act to facilitate the release of oxygen from the hemoglobin present in the claimed composition. If desired, a sterol from the following group is added: chlosterol, ergosterol, 7-dehydrocholesterol, $\alpha$ sitosterol, $\beta$sitosterol, $\gamma$ sitosterol, campesterol or mixtures thereof. Cholesterol is preferred. 0.1 to 10 mg. per cent of cholesterol may be added to the preparation to improve the stability of the composition. The preferred amount of cholesterol added to the composition is 1 mg. per cent.

Following this step the pH of the preparation is adjusted to 7.4 to 7.5 by the drop by drop addition of either HCl or sodium bicarbonate, depending upon the pH of the preparation. Any other suitable non toxic acidifying or alkalizing agent may be used in place of hydrochloric acid or sodium bicarbonate, however, the agents named are preferred.

Upon completion of this step, the compostion is again emulsified using either a colloid mill, sonification or other emulsifying technique known to those skilled in the art. This step produces emulsified droplets which contain the hemoglobin component. The droplets can range in size from less than 100 millimicrons to 15 microns and above; the preferred size is that of normal erythrocytes. However, the invention provides for the possibility that specific medical treatments may require that the size of the droplets be of smaller dimensions. If desired, enzymes, nutrients and drugs may be added to the coacervate phase of the composition or to the composition at this stage of manufacture.

If the manufacturing objective is to produce a composition that has the physiological properties of erythrocytes or packed red cells, the first step of that process consists of warming the preparation described immediately above. This step is accomplished by warming the preparation in a water bath or controlled oven to a temperature ranging from 15° to 50° C. for from 20 seconds to 3 hours in order to produce a cross linking of the albumin and lecithin of the composition. The effect of this process is a hardening of the surface of the emulsified droplets. The degree of hardness obtained is a function of the duration and temperature of the warming step. Thus, subjecting the composition for relatively shorter periods of time to higher temperatures will yield approximately the same degree of hardening of the emulsified droplet surfaces as subjecting the composition to lower temperatures for relatively longer periods of time. In point of fact, a spectrum of degrees of surface hardness is possible at this point of manufacture by varying the variables of time and temperature.

In this invention the degree of structuring or hardening of the surface of the emulsified droplets can range from fluid-like to semi-solid, i.e. gel-like to rigid. When the desired degree of surface hardness of the emulsified droplets has been achieved, the droplets are filtered from the emulsion. The filtrate is discarded. The droplets are removed from the filter bed, washed thoroughly with normal saline or other suitable solution and then dried by any of the conventional methods.

If desired, differing proportions of the dried preparation with differing degrees of shell hardness may be combined, during the process of reconstituting the preparation with normal saline or other suitable solutions. Alternatively, droplets of the same degree of surface hardness may be used in the process of reconstitution. In either formulation, the composition will possess special oxygen release properties, and will be capable of prompt, sustained and/or prolonged effects.

Cross linking may also be achieved through chemical means known to those skilled in the art, i.e., through the use of gluteraldehyde, etc. The method of heating is preferred in this invention. If it is desired to produce a product that has physiological properties similar to the cytoplasm of erythrocytes, the procedure described above is followed except that the hemoglobin component is omitted.

When the manufacturing steps are completed, the products, i.e., the oxygen transport solution, the blood substitute, or either of the derivative compositions, can be transfused into the circulatory system, where the individually described functions will be carried out: transport of physiological gases, restoration of blood pressure, transport of drugs and enzyme systems etc. Alternatively, each composition can be stored, preferably at from 4 to 10 degrees C. until needed. If the composition is to be infused into a human or animal following refrigerated storage, it should be warmed to body temperature (37 degrees C.) before infusion.

SPECIFIC EXAMPLES

Examples of how the claimed composition(s) of matter may be prepared follow:

Example 1

5% weight to volume proportions of albumin and lecithin are added to an amount of sterile water that will yield 100 mls of aqueous solution. The mixture is then thoroughly mixed by vortex mixer.

Following thorough mixing, the solution is stored undisturbed until the maximum yield of the coacervate phase of the coacervate system has been achieved. The storage step takes place at 4 degrees C.

When it is observed that the maximum yield of the coacervate phase has been achieved, the coacervate system is centrifuged until observation indicates that a clear division exists at the interface of the two phases of the coacervate system. The two phases are then separated by means of a separatory funnel. The equilibium phase is set aside for subsequent recombination with the coacervate phase. 15 grams of pyridoxalated-polymerized hemoglobin are then dispersed into the coacervate phase. After this step, 4% weight to volume di-phospho-glycerate is added and mixed into the coacervate phase.

The next step consists of recombining the equilibrium phase and the coacervate which contains the above named components and emulsifying the preparation, and adding that quantity of sodium chloride as will render the composition isotonic with human blood. At this point, 1 mg. per cent of urea is added. 1 mg. of cholesterol is added as the following step. The composition is then mixed vigorously until all additives are dispersed.

Following this step, the pH of the preparation is adjusted to 7.4 to 7.5 by the drop by drop addition of either HCl or sodium bicarbonate, depending upon the pH of the preparation at this stage of manufacture.

Upon completion of this step, the composition is again emulsified using a colloid mill. The resulting emulsified droplets which contain the hemoglobin component are prepared to be 7 microns in size.

Example 2

200 mls of 5% solution of albumin is added to 200 mls. of a 3% solution of lecithin and mixed thoroughly. The remaining steps of the procedure follow those of Example 1.

Example 3

The procedure of Example 1 is followed except that the urea adding step is omitted.

Example 4

The procedure of Example 1 is followed except that the cholesterol adding step is omitted.

Example 5

200 mls. of a 5% solution of albumin is added to 200 mls. of a 7% solution of lecithin and mixed thoroughly. The remaining steps of the procedure follow Example 1.

Example 6

200 mls. of a 3% solution of albumin is thoroughly mixed with 200 mls of a 3% solution of isolecithin. The solution is then stored undisturbed at 4 degrees C. for 24 hours. The remaining steps of the procedure follow Example 1.

Example 7

The procedure of Example 1 is followed except that the steps involving the addition of cholesterol and urea are omitted.

EXAMPLE 8

The procedure of Example 1 is followed to completion. The resulting composition is then subjected to a warming step. This consists of placing the solution in a water bath at 25 degrees C. for five minutes. At the end of this period the droplets of the composition are filtered from the emulsion, and washed thoroughly with normal saline solution and dried by conventional means. 100 mls of normal saline solution are added to the product resulting from this process thereby reconstituting a composition, the physiological properties of which are equivalent to the cytoplasm of packed red cells.

EXAMPLE 9

The procedure of Example 10 is followed except that the warming stage is carried out at 30 degrees C. for 1 minute.

Example 10

The procedure of Example 1 is followed except that 2% weight to volume of di-phospho-glycerate is used.

Example 11

The procedure of Example 1 is followed except that 1 mg. per cent of ergosterol is used in place of cholesterol.

Example 12

The procedure of Example 1 is followed except that the emulsified droplets in the finished product are prepared to be 100 millimicrons in size.

Example 13

The procedure follows Example 1 except that after the emulsification step, essential amino acids such as L-lysine, L-tryptophan, L-histidine, L-phenylalanine, L-leucine, L-isoleucine, L-threonine, L-valine, L-orgine, and L-methioine can be added in the amounts and mixtures as indicated by the needs of the individual situation.

Example 14

The procedure follows Example 1 except that hemoglobin and di-phospho-glycerate components are omitted from the manufacturing process. This example produces a composition which approximates the physiological properties of the cytoplasm of erythrocytes.

We claim:

1. A synthetic whole blood substitute, comprising a non-toxic two phase liquid system, both said phases being aqueous, one of said phases being a relatively non-polar coacervate phase, the other of said phases being a relatively polar liquid aqueous phase, said relatively non-polar coacervate phase being insoluble in and in equilibrium with said relatively polar liquid aqueous phase, and incorporated into said two phase system a hemoglobin component selected from the group consisting of polymerized hemoglobin, pyridoxylated-polymerized hemoglobin and mixtures thereof.

2. A synthetic whole blood substitute according to claim 1, wherein the relatively non-polar coacervate phase comprises from 0.05% to 99.5% by volume, of the two phase liquid system.

3. A synthetic whole blood substitute according to claim 1, wherein the phases are emulsified, whereby said relatively non-polar coacervate phase is in the form of coacervate droplets suspended in said relatively polar liquid aqueous phase.

4. A synthetic whole blood substitute according to claim 3, wherein said droplets are essentially of size within the range from 100 millimicrons to 10 microns.

5. A synthetic whole blood substitute according to claim 1, wherein the pH of the two phase liquid system is in the range of from 7.35 to 7.45.

6. A synthetic whole blood substitute according to claim 1, wherein the two aqueous phases comprise a protein or protein derivatives with surface active properties, an electrolyte, a surface active agent and water.

7. A synthetic whole blood substitute according to claim 6, wherein the protein or protein derivative is selected from albumin, gelatin or modified fluid gelatin.

8. A synthetic whole blood substitute according to claim 6, wherein the electrolyte is selected from sodium chloride, magnesium chloride, calcium chloride, potassium chloride and mixtures thereof.

9. A synthetic whole blood substitute according to claim 6, wherein the surface active agent is a phospholipid or a derivative thereof.

10. A synthetic whole blood substitute according to claim 9, wherein the phospholipid is selected from lecithin, cephalin, isolecithin, sphingomyelin, phosphatidyl serine, phosphatidic acid, phosphatidyl inositol, phosphatidyl choline or mixtures thereof.

11. A synthetic whole blood substitute as defined in any one of claims 1 to 10, wherein one or both of the aqueous phases include urea, electrolytes, hemoglobin, di-phosphogylcerate, sterols, or mixtures thereof.

12. A synthetic whole blood substitute according to claim 11, wherein the hemoglobin is pryidoxylated-polymerized hemoglobin.

13. A synthetic whole blood substitute according to claim 11, including di-phospho-glycerate.

14. A composition according to claim 11, wherein the sterol is selected from cholesterol, ergosterol, 7-dehydrocholesterol, $\alpha$ sitosterol, $\beta$ sitosterol, $\beta$ sitosterol or campesterol, or mixtures thereof.

15. A composition according to claim 11, wherein the electrolytes are selected from NaCl, KCl, MgCl, $CaCl_2$ or mixtures thereof.

16. A method of preparing a composition of matter which is useful as a blood substitute, said method characterized by the steps of (a) combining albumin and phospholipid in water; (b) thoroughly mixing the components; (c) storing said mixture undisturbed until the composition of step (a) separates into two layers, one above the other, the lower layer being a substantially non-polar coacervate phase, and the upper layer being an equilibrium water phase; (d) continuing the separation process until no increase in the volume of the coacervate phase can be observed; (e) centrifuging the composition until inspection reveals a clear demarcation of the two phases; (f) separating the two phases; and (g) adding a hemoglobin component selected from the group consisting of polymerized hemoglobin, pyridoxylated-polymerized hemoglobin and mixtures thereof, to the coacervate phase.

17. The method of claim 16, wherein the phospholipid is selected from lecithin, cephalin isolecithin, sphingomyelin, phosphatidyl serine, phosphatidic acid, phosphatidyl inositol, phosphatidyl choline, or mixtures thereof.

18. The method of claim 16, wherein the hemoglobin is pyridoxilated-polymerized hemoglobin.

19. The method of claim 18, including the step of adding from 0.5% to 10% weight to volume of di-phospho-glycerate to the coacervate phase, after the addition of pyridoxylated-polymerized hemoglobin.

20. The method of claim 19, including the further step of combining the equilibrium phase of the coacervate system and the associated coacervate phase now containing said additives.

21. The method of claim 20, including the further step of emulsifying the composition.

22. The method of claim 21, including the further step of adding an electrolyte in an amount that will render the isotonicity of the preparation equal to that of human blood.

23. The method of claim 22, wherein the electrolyte is selected from sodium chloride, potassium chloride, calcium chloride, magnesium chloride, or mixtures thereof.

24. The method of claim 23, including the further step of adding 0.1 to 1 mg. urea.

25. The method of claims 23 or 24, including the step of adding a sterol.

26. The method of claim 25, wherein the sterol is selected from cholesterol, ergosterol, 7-dehydrocholesterol, α sitosterol, β sitosterol, γ sitosterol, compesterol, and mixtures thereof.

27. The method of claim 25, including the step of adding from 0.1 to 10 mg. percent cholesterol.

28. The method of any one of claims 26 to 27, including the step of adjusting the pH of the preparation to 7.35 to 7.4 by the dropwise addition of either hydrochloric acid or sodium bicarbonate 29. The method of claim 28, including the further step of emulsifying the composition after said pH adjustment.

30. The method of claim 29, wherein the particles of said emulsion range from 100 millimicrons to 10 microns.

31. The method of any of claims 21, 29 or 30, wherein the emulsified composition is subjected to a process to harden the surfaces of the emulsified droplets contained within said emulsion.

32. The method of claim 31, wherein the hardening process is based upon either a physical or a chemical procedure.

33. The method of claim 32, wherein the physical process is comprised of a warming step.

34. The method of claim 33, wherein the composition is subjected to a warming procedure in which the composition is placed in a water bath, the temperature of which is from 15° C. to 50° C.

35. The method of claim 34, wherein the warming period is from 20 seconds to 3 hours.

36. The method of any one of claims 31 to 36, wherein the surface hardened droplets are filtered from the composition.

37. The method of claim 36, wherein the emulsified droplets containing the hemoglobin component are washed thoroughly.

38. The method of claim 37, wherein the composition is reconstituted by the addition of any physiologically suitable solution.

39. The method of claim 38, wherein the solution is normal saline solution.

40. A synthetic whole blood substitute, comprising a non-toxic two phase liquid system, both said phases being aqueous, one of said phases being a relatively non-polar coacervate phase, the other of said phases being a relatively polar liquid aqueous phase, said relatively non-polar coacervate phase being insoluble in and in equilibrium with said relatively polar liquid aqueous phase, and incorporated into said two phase system a hemoglobin component selected from the group consisting of stroma-free hemoglobin, polymerized hemoglobin, pyridoxylated-polymerized hemoglobin and mixtures thereof.

41. A method of preparing a composition of matter which is useful as a blood substitute, said method characterized by the steps of (a) combining albumin and phospholipid in water; (b) thoroughly mixing the components; (c) storing said mixture undisturbed until the composition of step (a) separates into two layers, one above the other, the lower layer being a substantially non-polar coacervate phase, and the upper layer being an equilibrium water phase; (d) continuing the separation process until no increase in the volume of the coacervate phase can be observed; (e) centrifuging the composition until inspection reveals a clear demarcation of the two phases; (f) separating the two phases; and (g) adding a hemoglobin component selected from the group consisting of stroma-free hemoglobin, polymerized hemoglobin, pyridoxylated-polymerized hemoglobin and mixtures thereof, to the coacervate phase.

* * * * *

UNITED STATES PATENT AND TRADEMARK OFFICE
CERTIFICATE OF CORRECTION

PATENT NO. : 4,738,952

DATED : April 19, 1988

INVENTOR(S) : Bernard Ecanow et al

It is certified that error appears in the above-identified patent and that said Letters Patent is hereby corrected as shown below:

Column 10, line 20, "β" (second occurrence) should read -- γ --.

Signed and Sealed this

Fourteenth Day of February, 1989

Attest:

DONALD J. QUIGG

*Attesting Officer*     *Commissioner of Patents and Trademarks*